(12) United States Patent
Ekblom et al.

(10) Patent No.: US 8,524,928 B2
(45) Date of Patent: Sep. 3, 2013

(54) HYDROGENATION PROCESS

(75) Inventors: Jari Ekblom, Raisio (FI); Antti Hamunen, Turku (FI); Rami Hartonen, Turku (FI); Marko Hirvijärvi, Raisio (FI); Juha Holma, Turku (FI); Juha Orte, Raisio (FI)

(73) Assignee: Raisio Nutrition Ltd., Raisio (FI)

( * ) Notice: Subject to any disclaimer, the term of this patent is extended or adjusted under 35 U.S.C. 154(b) by 281 days.

(21) Appl. No.: 13/054,031

(22) PCT Filed: Jul. 24, 2009

(86) PCT No.: PCT/FI2009/000070
§ 371 (c)(1),
(2), (4) Date: Mar. 3, 2011

(87) PCT Pub. No.: WO2010/010228
PCT Pub. Date: Jan. 28, 2010

(65) Prior Publication Data
US 2011/0184197 A1 Jul. 28, 2011

Related U.S. Application Data

(60) Provisional application No. 61/083,657, filed on Jul. 25, 2008, provisional application No. 61/083,647, filed on Jul. 25, 2008.

(51) Int. Cl.
*C07J 9/00* (2006.01)

(52) U.S. Cl.
USPC .................................... 552/545; 552/544

(58) Field of Classification Search
USPC .................................... 552/544, 545
See application file for complete search history.

(56) References Cited

FOREIGN PATENT DOCUMENTS
EP    1 693 376  A2    8/2006

OTHER PUBLICATIONS

Minna Lindroos, et al., "Catalyst Deactivation in Selective Hydrogenation of β-Sitosterol to β-Sitostanol over Palladium", Catalysis in Organic Reactions, 2002, pp. 587-594.

*Primary Examiner* — Barbara P Badio
(74) *Attorney, Agent, or Firm* — Arent Fox LLP

(57) ABSTRACT

The invention relates to an effective process for producing plant stanol by hydrogenating plant sterol in an organic solvent at a hydrogen pressure of 1-200 bar in the presence of a hydrogenation catalyst.

36 Claims, No Drawings

HYDROGENATION PROCESS

CROSS-REFERENCE TO RELATED APPLICATION

This application is a National Stage entry of International Application No. PCT/FI2009/000070, filed Jul. 24, 2009, which claims priority to U.S. Patent Application 61/083,657, filed Jul. 25, 2008, and U.S. Patent Application 61/083,647, filed Jul. 25, 2008. The disclosure of the prior applications are hereby incorporated in their entirety by reference.

Plant sterols are compounds appearing in plant material and they are commercially isolated from edible oil refining residues or from crude tall oil, which is a wood pulping by-product stream. The plant sterols consist typically of several individual compounds; campesterol, sitosterol, stigmasterol and sitostanol being the most common chemical structures.

The plant sterol production process from edible oil refining residues ("deodoriser distillates, DOD") typically comprises following steps:
1. esterification of free acids and liberation of sterols from sterol esters
2. optional evaporation of the light fractions to remain the sterols in the residue
3. optional evaporation of the free sterol fraction
4. crystallisation of free sterols from a sterol rich fraction obtained from step 1, 2 or 3, and
5. optional recrystallisation of the sterols to make the pure sterol product.

In the optional recrystallisation process mentioned above the used crystallisation solvents are typically aliphatic hydrocarbons wherein some lower alcohol (methanol or ethanol) and water has been added. Alternatively ethanol as such can be used.

In plant sterol production from wood pulping by-product streams the actual raw material is tall oil pitch ("TOP"). Tall oil pitch is the distillation residue from the tall oil refining process which produces fatty acids and resin acids for the chemical industry. Tall oil is the acidulated product of organic extractives recovered from cooking liquor ("black liquor") produced in the wood pulping process.

The sterol extraction process from tall oil pitch typically comprises
1. liberation of sterols from sterol esters by saponification
2. optional acidulation or neutralization of free acids present
3. evaporation of the light fraction from the dried saponificated mixture from step 1 or from the acidulated or neutralized mixture from step 2 to remain the sterols in the residue
4. evaporation of the residue of step 3 to obtain a sterol rich fraction
5. crystallisation of the sterols from the sterol rich fraction, and
6. optional recrystallisation of the sterols to make the pure sterol product.

The crystallisation and/or the optional recrystallisation solvent in the process of isolating sterols from TOP is typically an aliphatic hydrocarbon or a mixture of aliphatic hydrocarbons wherein some water and lower alcohol (methanol or ethanol) is added or a ketone based solvent (typically a mixture of methyl ethyl ketone, lower alcohol and water).

During recent years plant sterol based compounds have become common as cholesterol lowering ingredients in so called functional foods. In these applications these compounds are added into food products e.g. spreads and yoghurts in free form or esterified with fatty acids, typically derived from vegetable oils. In one preferred mode of application these sterols are prior to addition into foods or prior to esterification saturated by catalytic hydrogenation to produce plant stanols. Plant stanols are thus compounds in which no double bonds found in the original sterol structure can be found due to hydrogen addition into the double bonds of the sterol molecule. The advantages of stanols over sterols include e.g. better stability against oxidation and lower absorbability into the blood circulation from the digestive tract, which have been shown to be highly desirable properties.

The commercial production of stanols takes place in a separate process using isolated and purified sterols as the substrate in the hydrogenation process. This purified sterol is dissolved into an organic solvent (n-propanol or isopropanol), the solution is inertised, a hydrogenation catalyst is added and a hydrogen stream is led into the reaction mixture at suitable reaction conditions. Typically the hydrogenation process is catalyzed by palladium (a precious metal), which generally is dispersed on charcoal support material. In an optimal case the hydrogenation reaction is rapid, goes to complete conversion and as a result of the reaction only saturated sterols i.e. stanols are formed. However, in general there are many problems with the process.

Firstly, the conversion reaction produces in addition to the desired stanols also by-products. Typical by-products in sterol hydrogenation are stanones (the OH-group in position 3 of the sterol backbone is converted to a ketone group due to double bond migration) and stanes (the OH-group cleaves away, and generally the remaining unsaturated sterol residue is saturated at the used reaction conditions). If the amount of these by-products is high, the selectivity of the reaction is poor.

Secondly, the purified sterol used as starting material for the hydrogenation still contains trace impurities derived e.g. from the raw materials used (e.g. DOD and TOP), and these trace impurities tend to deactivate or poison the catalyst. This deactivation retards the hydrogenation reaction or may stop it practically. The retardation (i.e. low reaction activity) means longer reaction times and hence in commercial production reduced production capacity. In order to avoid this retarded conversion rate one approach is to use additional amounts of precious metal catalysts. However, because these catalysts are extremely expensive this leads to increased production costs.

In the present invention the problems connected with low activity and low selectivity are solved by using one or more of the following: optimal catalyst choice, proper pre-purification of the sterol used as starting material for the hydrogenation and by choosing optimal reaction conditions.

It was realised that a process for producing plant stanol by hydrogenating plant sterol in an organic solvent at a hydrogen pressure of 1-200 bar should take place in the presence of a hydrogenation catalyst comprising silicon, which is preferably in the form of silicon dioxide (silica) and more preferably in the form of zeolite. Advantageously, the process also includes a step of pre-purifying the plant sterol before performing the hydrogenation.

Surprisingly, it was also noticed that zeolite as support material in a hydrogenation process for producing plant stanol was very effective and produced only low levels of by-products.

1. Choice of Optimal Catalyst Type

It has now surprisingly been discovered that much better selectivity in sterol hydrogenation is achieved by using a hydrogenation catalyst on a support material comprising silicon (Si) instead of prior known charcoal support. Preferably, the support material comprises silicon in the form of silicon dioxide (silica). Advantageously, the support material also comprises aluminium (Al), preferably in the form of aluminium oxide (alumina). More preferably, the support material comprises silicon and aluminium in the form of zeolite. Advantageously, the support material comprises at least 25%, preferably at least 50%, more preferably at least 75% and most preferably at least 95% zeolite by dry weight of the support material. Usually, the catalyst comprises at least one noble metal selected from the group consisting of palladium, platinum, ruthenium, rubidium, iridium and rhodium. Preferably, it comprises essentially palladium (Pd), preferably at least 90% and more preferably at least 95% palladium by dry weight of the catalyst. Si:Al ratio of the support material is preferably 1-400:1, usually below 100:1 and more preferably 1-5:1. The support material may thus comprise at least one of zeolite, silica and non-crystallised silica-alumina. Preferably the support material comprises zeolite, which advantageously is crystalline, hydrated aluminosilicate with a framework structure. The zeolite has silica:alumina ratio of at least 2:1, preferably 2-200:1, more preferably 2-50:1 and even more preferably 2-10:1. Y (preferably USY) zeolites, ZSM-5, mordenite and especially their hydrogen forms have been found highly suitable of the many zeolite types. Preferably, the palladium/zeolite (Pd/Z) hydrogenation catalyst (zeolite doped with palladium) applied in sterol hydrogenation has a Pd content of 0.5-7% by dry weight, a mean particle size of 60-200 μm, a size distribution with more than 90% of the particles 50-300 μm and a specific surface area of 80-160 $m^2/g$.

2. Proper Pre-Purification

It has now been discovered that by treating dissolved sterols with certain type of absorbents and/or adsorbents the amount of trace impurities retarding the reaction is significantly reduced whereby the reaction time needed for complete reaction is shortened and the amount of catalyst needed for the reaction is reduced.

Suitable pre-purification options for treating sterols before the hydrogenation reaction include treatment with
  activated charcoal
  charcoal and chelating agent (e.g. citrate, EDTA)
  bleaching earth/silica
  a mixture of activated charcoal and bleaching earth/silica
  a cellulose based absorbent
  polyelectrolytes and ion exchange fibers (e.g. polyacrylate)
  zeolite Of these, steam and acid activated charcoal are very suitable, preferably the former.

3. Proper Hydrogenation Conditions

Optimal conditions in order to avoid by-product formation include:
  high hydrogen pressure during hydrogenation reaction and optimal solvent composition.

The hydrogen pressure is 1-200 bar, preferably 3-200 bar, more preferably 10-200 bar and most preferably 30-200 bar.

It has now surprisingly been discovered that hydrogenation e.g. in solvent mixtures which consist of aliphatic or acyclic hydrocarbons, lower alkanol and water give clearly improved selectivity than currently used propanol. Preferably the solvent is a mixture of hydrocarbon (2-98%), alkanol (2-98%) and water (0.1-5%), more preferably a mixture of hydrocarbon (70-97%), alkanol (2-28%) and water (1-10%), and most preferably a mixture of hydrocarbon (85-90%), alkanol (5-10%) and water (1-5%). Preferably the hydrocarbon is a C5-C12 aliphatic or acyclic hydrocarbon, or a mixture of such hydrocarbons, more preferably it is heptane. Preferably the alkanol is a C1-C3 alkanol, more preferably methanol and/or ethanol, and most preferably methanol. All % here are % by weight. This solvent composition is also often used in sterol crystallisation when isolating sterols. The solvent containing hydrocarbon, alcohol and water can also comprise compositions where the alcohol forms the major part of the solvent.

EXAMPLE 1

Comparison of the Use of Different Catalysts and the Effect of Charchoal Pre-Purification in Sterol Hydrogenation The tested catalysts were:

| | |
|---|---|
| Pd/Z | 3% Pd on zeolite, moisture content 2.1%, specific surface area 120 $m^2/g$, particle size distribution: max 2% < 63 μm; min 95% < 250 μm |
| Pd/S | 4% Pd on silica, moisture content 2.9% |
| Pd/C | 5% Pd on activated charcoal, moisture content 55% |

The following hydrogenation reactions were performed by using wood sterols (total sterol content 98%) as substrate. The substrate was dissolved to a 24 wt % sterol solution in n-propanol by heating.

In cases where pre-purification was applied, charcoal (Norit SX1G, 3 wt % of the sterol amount) was mixed for 30 minutes and removed by filtration.

For hydrogenation, the solution was transferred into a pressure vessel. The vessel was inertised from oxygen with nitrogen flushes, the catalyst was added dispersed in n-propanol through an inlet funnel whereafter the reaction temperature was kept at 80° C. The hydrogen pressure was maintained during the reaction at 4 bar. The ratio of palladium to sterol was 0.05%.

The hydrogenation time was measured from the addition of the catalyst until the hydrogen uptake ceased. The completion of the hydrogenation reaction was also verified by analysis of sterols and stanols. The amounts of sterols, stanols, stanes, stanones and other impurities were all analyzed by GC.

The results are shown in Table 1.

TABLE 1

| | Test no | | | | | |
|---|---|---|---|---|---|---|
| | 1 | 2 | 3 | 4 | 5 | 6 |
| Catalyst type | Pd/Z | Pd/Z | Pd/S | Pd/S | Pd/C | Pd/C |
| Charcoal purification | yes | no | yes | no | yes | no |
| Reaction time, min | 60 | 120 | 60 | 120 | 60 | 120 |
| Total unreacted sterols, % | 2.5 | 3.0 | 3.0 | 3.6 | 2.1 | 2.9 |
| Total stanols, % | 95.5 | 95.1 | 94.2 | 93.4 | 91.0 | 89.9 |
| Stanes, % | 0.1 | 0.2 | 0.4 | 0.6 | 4.5 | 4.6 |
| Stanones, % | 1.2 | 0.6 | 1.2 | 1.4 | 1.9 | 2.2 |
| Other impurities, % | 0.6 | 1.2 | 1.2 | 1.0 | 0.5 | 0.4 |
| Total impurities, % | 1.9 | 2.0 | 2.8 | 3.0 | 6.9 | 7.2 |

The results show that the Pd/Z catalyst worked clearly more selectively than the used Pd/C catalysts in the sterol hydrogenation reaction. Pre-purification with activated charcoal increased reaction rates significantly. Pd/S was better than Pd/C but not as good as Pd/Z.

EXAMPLE 2

Effect of Different Pre-Purification Treatments on the Results of Hydrogenation when Using Pd/Z Catalyst The hydrogenations and purifications were performed at the same conditions as used in Example 1.

The absorbents and/or adsorbents were:
Trial 1: Non (Example 1 test 2)
Trial 2: Charcoal Norit SXG1 (3 wt % of the amount of sterol) (Example 1 test 1)
Trial 3: Tonsil Optimum FF (3 wt %)
Trial 4: Charcoal Norit SXG1 (3 wt %)+EDTA in sodium salt form (1.5 wt %)
Trial 5: Charcoal Norit SXG1 (3 wt %)+dispersed pinewood pulp (1.5 wt %)
Trial 6: Ionic polyethylene acrylate fiber SMOPEX in sodium salt form (3 wt %)
Trial 7: Used catalyst from Trial 1

TABLE 2

| | Trial no | | | | | | |
|---|---|---|---|---|---|---|---|
| | 1 | 2 | 3 | 4 | 5 | 6 | 7 |
| Reaction time, min | 120 | 60 | 70 | 55 | 55 | 90 | 70 |
| Total unreacted sterols, % | 3.0 | 2.5 | 3.2 | 2.5 | 3.0 | 3.4 | 3.0 |
| Total stanols, % | 95.1 | 95.5 | 94.7 | 94.8 | 95.0 | 94.0 | 95.2 |
| Stanes, % | 0.2 | 0.1 | 0.3 | 0.4 | 0.1 | 0.3 | 0.3 |
| Stanones, % | 0.6 | 1.2 | 0.5 | 1.5 | 0.7 | 1.2 | 0.7 |
| Other impurities, % | 1.2 | 0.6 | 1.3 | 0.8 | 1.2 | 1.0 | 0.8 |
| Total impurities, % | 2.0 | 1.9 | 2.1 | 2.7 | 2.0 | 2.5 | 1.8 |

Compared to the first trial (Example 1, test 2) all the pre-purification treatments led to an increased reaction activity, which is shown as shorter reaction time needed to get the reaction close to completion.

EXAMPLE 3

Effect of the Process Conditions

The trial no 2 of Example 2 was repeated by using more rigid reaction conditions:

Hydrogen pressure 35 bar and reaction temperature 90° C.

The reaction was completed in 30 minutes. The composition of the reaction product was practically identical with the result achieved in Example 2, trial 2.

EXAMPLE 4

Effect of Solvent Composition

Instead of n-propanol (n-p), mixture of heptane (h, 87%), methanol (m, 9%) and water (w, 4%) or mixture of heptane (h, 20%), ethanol (e, 76%) 4 and water (w, 4%) was used as the solvent.

Pre-purification with charcoal was performed as in Example 2, trial 2 (Norit SXG1, 3 wt % of the amount of sterol).

The sterol concentration in the solution was 10%. Reaction conditions: hydrogen pressure 35 bar and temperature 90° C.

Note: The reference trials (R1=Example 1, test 1 and R2=Example 1, test 5) in Table 3 were done at the reaction conditions of Example 1.

TABLE 3

| | Trial number | | | | | |
|---|---|---|---|---|---|---|
| | R1 | 1 | 2 | R2 | 3 | 4 |
| Catalyst carrier | Z | Z | Z | C | C | C |
| Solvent | n-p | hmw | hew | n-p | hmw | hew |
| Reaction time, min | 60 | 60 | 60 | 60 | 60 | 60 |
| Total unreacted sterols, % | 2.5 | 1.8 | 1.6 | 2.1 | 1.8 | 1.9 |
| Total stanols, % | 95.5 | 96.5 | 96.3 | 91.0 | 94.0 | 94.3 |
| Stanes, % | 0.1 | 0.1 | 0.1 | 4.5 | 1.9 | 1.8 |
| Stanones, % | 1.2 | 0.5 | 0.7 | 1.9 | 1.5 | 1.4 |
| Other impurities, % | 0.6 | 1.1 | 1.3 | 0.5 | 0.8 | 0.6 |
| Total impurities, % | 1.9 | 0.7 | 1.1 | 6.9 | 4.2 | 3.8 |

The results show improved selectivity when changing the solvent composition and the hydrogenation conditions.

The invention relates to a process for producing plant stanol by hydrogenating plant sterol in an organic solvent at a hydrogen pressure of 1-200 bar in the presence of a hydrogenation catalyst on a support material characterised in that the support material comprises silicon (Si).

The process preferably also includes a step of pre-purifying the plant sterol before performing the hydrogenation.

In the process the hydrogen pressure is preferably 3-200 bar, more preferably 10-200 bar and even more preferably 30-200.

In the process the hydrogenation catalyst preferably comprises at least one from the group of palladium, platinum, ruthenium, rubidium, iridium and rhodium.

In the process the hydrogenation catalyst preferably comprises essentially palladium, more preferably at least 90% and even more preferably at least 95% palladium by dry weight of the catalyst.

In the process the support material preferably comprises silicon in the form of silicon dioxide (silica).

In the process the support material preferably further comprises aluminium (Al). Advantageously the aluminium is in the form of aluminium oxide (alumina).

In the process the support material preferably comprises silicon in the form of zeolite.

In the process the support material preferably contains at least 25%, more preferably at least 50%, even more preferably at least 75% and most preferably at least 95% zeolite by dry weight of the support material.

In the process the Si:Al ratio of the support material preferably is 1-400:1, more preferably 1-100:1 and even more preferably 1-5:1.

In process preferably the silica:alumina ratio of the support material is at least 2:1, more preferably 2-200:1, even more preferably 2-50:1 and most preferably 2-10:1.

In the process the pre-purifying is preferably performed in the organic solvent with an absorbent and/or adsorbent.

In the process the pre-purifying is preferably performed in the organic solvent with activated charcoal, more preferably with steam activated charcoal.

In the process the organic solvent preferably comprises at least one hydrocarbon, more preferably at least one C5-C12 aliphatic or acyclic hydrocarbon and even more preferably heptane.

In the process the organic solvent preferably comprises at least one C1-C3 alkanol, more preferably methanol and/or ethanol, and even more preferably methanol.

In process the organic solvent preferably comprises a mixture of hydrocarbon (2-98% by weight), alkanol (2-98% by weight) and water (0.1-5% by weight), more preferably a mixture of hydrocarbon (70-97% by weight), alkanol (2-28% by weight) and water (1-10% by weight), and even more preferably a mixture of hydrocarbon (85-90% by weight), alkanol (5-10% by weight) and water (1-5% by weight).

The invention claimed is:

1. A process for producing plant stanol by hydrogenating plant sterol in an organic solvent at a hydrogen pressure of 1-200 bar in the presence of a hydrogenation catalyst on a support material characterised in that
the support material comprises silicon (Si) and
the process includes a step of pre-purifying the plant sterol before performing the hydrogenation.

2. The process according to claim 1 characterised in that the hydrogen pressure is 3-200 bar.

3. The process according to claim 1 characterised in that the hydrogenation catalyst comprises at least one from the group of palladium, platinum, ruthenium, rubidium, iridium and rhodium.

4. The process according to claim 1 characterised in that the hydrogenation catalyst comprises essentially palladium.

5. The process according to claim 1 characterised in that the support material comprises silicon in the form of silicon dioxide (silica).

6. The process according to claim 1 characterised in that the support material further comprises aluminium (Al).

7. The process according to claim 1 characterised in that the support material comprises silicon in the form of zeolite.

8. The process according to claim 7, characterised in that the support material comprises at least 25% zeolite by dry weight of the support material.

9. The process according to claim 6, characterised in that the Si:Al ratio of the support material is 1-400:1.

10. The process according to claim 1 characterised in that the pre-purifying is performed in the organic solvent with an absorbent and/or adsorbent.

11. The process according to claim 1 characterised in that the pre-purifying is performed in the organic solvent with activated charcoal.

12. The process according to claim 1 characterised in that the organic solvent comprises at least one hydrocarbon.

13. The process according to claim 1 characterised in that the organic solvent comprises at least one C1-C3 alkanol.

14. The process according to claim 1 characterised in that the organic solvent comprises a mixture of hydrocarbon, alkanol.

15. The process according to claim 2, characterised in that the hydrogen pressure is 10-200 bar.

16. The process according to claim 2, characterised in that the hydrogen pressure is 30-200 bar.

17. The process according to claim 4, characterised in that the hydrogenation catalyst comprises at least 90% palladium by dry weight of the catalyst.

18. The process according to claim 4, characterised in that the hydrogenation catalyst comprises at least 95% palladium by dry weight of the catalyst.

19. The process according to claim 6, characterised in that the aluminium (Al) is in the form of aluminium oxide (alumina).

20. The process according to claim 7, characterised in that the support material comprises at least 50% zeolite by dry weight of the support material.

21. The process according to claim 7, characterised in that the support material comprises at least 75% zeolite by dry weight of the support material.

22. The process according to claim 7, characterised in that the support material comprises at least 95% zeolite by dry weight of the support material.

23. The process according to claim 9, characterised in that the Si:Al ratio of the support material is 1-100:1.

24. The process according to claim 9, characterised in that the Si:Al ratio of the support material is 1-5:1.

25. The process according to claim 19, characterised in that the silica:alumina ratio of the support material is at least 2:1.

26. The process according to claim 19, characterised in that the silica:alumina ratio of the support material is 2-200:1.

27. The process according to claim 19, characterised in that the silica:alumina ratio of the support material is 2-50:1.

28. The process according to claim 19, characterised in that the silica:alumina ratio of the support material is 2-10:1.

29. The process according to claim 1, characterised in that the step of pre-purifying is performed in the organic solvent with steam activated charcoal.

30. The process according to claim 12, characterised in that the organic solvent comprises at least one C5-C12 aliphatic or acyclic hydrocarbon.

31. The process according to claim 12, characterised in that the organic solvent comprises heptane.

32. The process according to claim 13, characterised in that the organic solvent comprises methanol and/or ethanol.

33. The process according to claim 13, characterised in that the organic solvent comprises methanol.

34. The process according to claim 14, characterised in that the organic solvent comprises a mixture of hydrocarbon (2-98% by weight), alkanol (2-98% by weight) and water (0.1-5% by weight).

35. The process according to claim 14, characterised in that the organic solvent comprises a mixture of hydrocarbon (70-97% by weight), alkanol (2-28% by weight) and water (1-10% by weight).

36. The process according to claim 14, characterised in that the organic solvent comprises a mixture of hydrocarbon (85-90% by weight), alkanol (5-10% by weight) and water (1-5% by weight).

* * * * *